United States Patent
Joo et al.

(10) Patent No.: US 12,396,983 B2
(45) Date of Patent: Aug. 26, 2025

(54) COMPOSITION COMPRISING RILMENIDINE COMPOUND AS ACTIVE INGREDIENT FOR TREATMENT OF FRAGILE X SYNDROME OR RELATED DEVELOPMENTAL DISABILITY

(71) Applicant: NEUROVENTI, Seoul (KR)

(72) Inventors: Sohyun Joo, Seoul (KR); Chanyoung Shin, Seoul (KR); Sejin Jeon, Seoul (KR); Taejin Ahn, Seoul (KR)

(73) Assignee: NEUROVENTI, Seoul (KR)

( * ) Notice: Subject to any disclaimer, the term of this patent is extended or adjusted under 35 U.S.C. 154(b) by 594 days.

(21) Appl. No.: 17/760,206

(22) PCT Filed: Feb. 5, 2021

(86) PCT No.: PCT/KR2021/001548
§ 371 (c)(1),
(2) Date: Aug. 5, 2022

(87) PCT Pub. No.: WO2021/158059
PCT Pub. Date: Aug. 12, 2021

(65) Prior Publication Data
US 2023/0055339 A1    Feb. 23, 2023

(30) Foreign Application Priority Data
Feb. 7, 2020   (KR) .................. 10-2020-0014635

(51) Int. Cl.
*A61K 31/421*   (2006.01)
*A61P 25/18*    (2006.01)

(52) U.S. Cl.
CPC ............ *A61K 31/421* (2013.01); *A61P 25/18* (2018.01)

(58) Field of Classification Search
CPC .......................... A61K 31/421; A61P 25/18
See application file for complete search history.

(56) References Cited

U.S. PATENT DOCUMENTS 5,605,911 A * 2/1997 Olney .................. A61K 45/06
                                                          514/315
2005/0165080 A1   7/2005 Rupp et al.

FOREIGN PATENT DOCUMENTS

| CN | 1927381      | 3/2007  |
| KR | 20160078956  | 7/2016  |
| KR | 20190094167  | 8/2019  |
| KR | 20190108104  | 9/2019  |
| KR | 20190121569  | 10/2019 |
| WO | WO 2004/000312 | 12/2003 |

OTHER PUBLICATIONS

He et al., "An integrated transcriptomic analysis of autism spectrum disorder" *Scientific Reports* 2019, 9:11818, 1-9.
International Search Report and Written Opinion issued in Corresponding PCT Application No. PCT/KR2021/001548, dated May 11, 2021 (English Translation provided).
Manfredini et al., "Mitochondrial dysfunction is associated with long-term cognitive impairment in an animal sepsis model" *Clinical Science* 2019,133, 1993-2004.
Underwood et al., "An open-label study to assess the feasibility and tolerability of rilmenidine for the treatment of Huntington's disease" *J Neurol* 2017, 264:2457-2463.

* cited by examiner

*Primary Examiner* — Kamal A Saeed
(74) *Attorney, Agent, or Firm* — NORTON ROSE FULBRIGHT US LLP

(57) ABSTRACT

The present invention relates to a composition for preventing, improving, or treating fragile X syndrome, fragile X syndrome-related developmental disorders, autism spectrum disorder or schizophrenia, comprising rilmenidine, a rilmenidine metabolite, or a pharmaceutically acceptable salt thereof.

5 Claims, 5 Drawing Sheets

COMPOSITION COMPRISING RILMENIDINE COMPOUND AS ACTIVE INGREDIENT FOR TREATMENT OF FRAGILE X SYNDROME OR RELATED DEVELOPMENTAL DISABILITY

CROSS-REFERENCE TO RELATED APPLICATION

This application is a national phase application under 35 U.S.C. § 371 of International Application No. PCT/KR2021/001548, filed Feb. 5, 2021, which claims priority to and the benefit of Korean Application No. 10-2020-0014635, filed Feb. 7, 2020. The contents of the referenced patent applications are incorporated into the present application by reference.

FIELD OF THE DISCLOSURE

The present invention relates to a composition for preventing, improving, or treating fragile X syndrome, any fragile X syndrome-related developmental disorders, autism spectrum disorder, or schizophrenia, comprising rilmenidine, a rilmenidine metabolite, or a pharmaceutically acceptable salt thereof.

DESCRIPTION OF RELATED ART

Fragile X syndrome (FXS) is caused by a decrease in the Fmr1 (fragile x mental retardation 1) gene functioning due to the amplification of the number of repeats of the CGG triple base at the 27.3 chromosomal location of the X gene. It also causes a lack of FMRP (Fragile X mental retardation protein), a protein produced through encoding the above gene. Considering that it is a disease caused by mutations in the X chromosome, the prevalence is about 1.5 times higher in men than in women. Fragile X syndrome has various comorbidities, and these diseases are mainly related to cranial nerve diseases. About 50% of patients have Attention Deficit Hyperactivity Disorder (ADHD) or autism, and there are also many patients with mental retardation, impulsivity, or language and cognitive disorders.

For research on the treatment of fragile X syndrome, mice lacking the Fmr1 gene, a causative gene, were invented in 1994 and are still widely used. This animal model has phenotypes in several behavioral aspects, such as hyperactivity, lack of sociability, repetitive behaviors, anxiety disorder, and cognitive decline depending on the strain of the mouse being used.

Most of the drugs used for the treatment of fragile X syndrome target group 1 metabolic-oriented glutamate receptors or inducible amino acid receptors to correct the imbalance of glutamate and glutamate receptors. In addition, they also target several proteins such as MMP9, MAP1B, PSD95, CaMKII, Arc, and STEP, which are involved in the FMRP protein production. However, difficulties in showing a therapeutic effect for just one symptom or failing in clinical trials have been reported.

On the other hand, Autism Spectrum Disorder (ASD) refers to a developmental disorder whose main symptoms include limitation of the range of behavioral interests, impairment of verbal and non-verbal communication, or decreased ability to understand social interaction. Previously, it was called autism, but recently, the diagnosis was revised to autism spectrum disorder, emphasizing that the degree and prognosis of autism are very diverse. ASD includes autism and pervasive developmental disorders (PDD), Asperger's Syndrome, Rett's Disorder, Childhood Disintegrative Disorder, and Pervasive Developmental Disorder (PDD NOS), not elsewhere classified. ASD is characterized by developmental delay or abnormal functioning before 3 years of age in at least one of the following areas: quality defects in social interaction and communication, hyperactivity, and restrictive/repetitive behaviors. In addition to the main symptoms, it is accompanied by symptoms of intellectual disability, sleep disturbances, gastrointestinal problems, epilepsy, or impulsive behaviors. However, the physiological cause and mechanism of the pathology of autism are not yet known, and the method for diagnosing ASD through molecular biological or pathological indicators has not yet been established. Thus, no drug is yet available to treat the cause of ASD, and only symptomatic drug treatment is given for accompanying symptoms such as epilepsy, self-harm, aggressive behavior, anxiety, or emotional disorder. Moreover, no drug is currently available that treats the core symptoms of ASD which are social deficits, and repetitive behaviors. Currently, research on the treatment response to existing psychiatric drugs such as fluoxetine and clozapine is being conducted at a rudimentary level. Experimental drugs such as D-cycloserine, oxytocin, Methallothionein I/II, and Gold are also utilized, but systematic efficacy studies have not been reported.

Schizophrenia is a typical psychiatric disorder, and it is a collection (syndrome) of various psychotic symptoms in which complex symptoms appear in various areas such as speech, behavior, emotion, and cognition, which are related and derived from a thinking disorder as the main pathology. Conventional antipsychotic drugs used to relieve symptoms of schizophrenia improve the quality of life of patients to some extent, but they do not induce complete cure and their use is limited due to side effects. Therefore, these drugs have limited therapeutic value in the management of schizophrenia, and the development of new drugs with improved efficacy and side effects is required.

SUMMARY

Efforts were being made to develop a therapeutic agent that can obtain a direct therapeutic effect for various symptoms of fragile X syndrome, any fragile X syndrome-related developmental disorders, autism spectrum disorder, or schizophrenia. Accordingly, the present invention was completed by confirming that Fmr1-deficient fragile X syndrome animal models, Cntnap2-deficient animal models, MK-801 drug-induced animal models, and schizophrenia animal models were alleviated in terms of sociability and pre-pulse inhibition (PPI) by the administration of rilmenidine.

Accordingly, one of the objectives of the present invention provides a pharmaceutical composition comprising rilmenidine, a rilmenidine metabolite, or a pharmaceutically acceptable salt thereof which is capable of preventing or treating fragile X syndrome (FXS), any fragile X syndrome-related developmental disorders, autism spectrum, a disorder or schizophrenia However, the technical problem to be achieved by the present invention is not limited to the above-mentioned problems, and other problems not mentioned will be clearly understood by those skilled in the art from the following detailed description.

To achieve the above-mentioned objective, the present invention can provide a composition for preventing, improving, or treating fragile X syndrome, any fragile X syndrome-related developmental disorders, autism spectrum disorder, or schizophrenia comprising rilmenidine, a rilmenidine metabolite, or a pharmaceutically acceptable salt thereof.

In addition, the present invention also provides a health functional food composition for preventing or improving fragile X syndrome, any fragile X syndrome-related developmental disorders, autism spectrum disorder, or schizophrenia comprising rilmenidine, a rilmenidine metabolite, or a pharmaceutically acceptable salt thereof.

Rilmenidine may be a compound represented by the following formula (1):

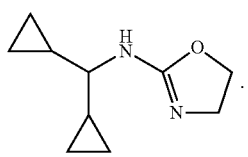

[Formula 1]

In the present invention, fragile X syndrome may be accompanied by one or more symptoms ranging from repetitive behaviors, hyperactivity, reduced learning ability, lack of sociability, impulsivity, and anxiety symptoms.

In the present invention, fragile X syndrome-related developmental disorders may include any one or more disorders from the group consisting of attention deficit hyperactivity disorder (ADHD), autism spectrum disorder (ASD), intellectual disability, cognitive impairment, impulse control and anxiety disorders.

In the present invention, autism spectrum disorder may be accompanied by one or more symptoms ranging from hyperactivity or lack of sociability.

The composition of the present invention has an effect of improving social behaviors and pre-pulse inhibition (PPI) in Fmr1-deficient fragile X syndrome animal models, Cntnap2-deficient animal models, MK-801 drug-induced autism animal models, and schizophrenia animal models. Thus, the present composition can be used as a preventive or therapeutic agent for fragile X syndrome, any developmental disorders related to fragile X syndrome, autism spectrum disorder, or schizophrenia. In addition, the present invention can provide beneficial effects in a single drug compared to administering various drugs to alleviate several symptoms. In addition, the side effects caused by the administration of many drugs can be avoided and the economic burden can be reduced. Furthermore, since fragile X syndrome and the like have homology with various mental developmental diseases such as cognitive impairment, attention deficit hyperactivity disorder, impulsivity, and autism, the present invention can be used in the treatment of fragile X syndrome, ASD or Schizophrenia, as well as in the treatment of various neurodevelopmental disorders.

DETAILED DESCRIPTION OF THE INVENTION

Figure 1:
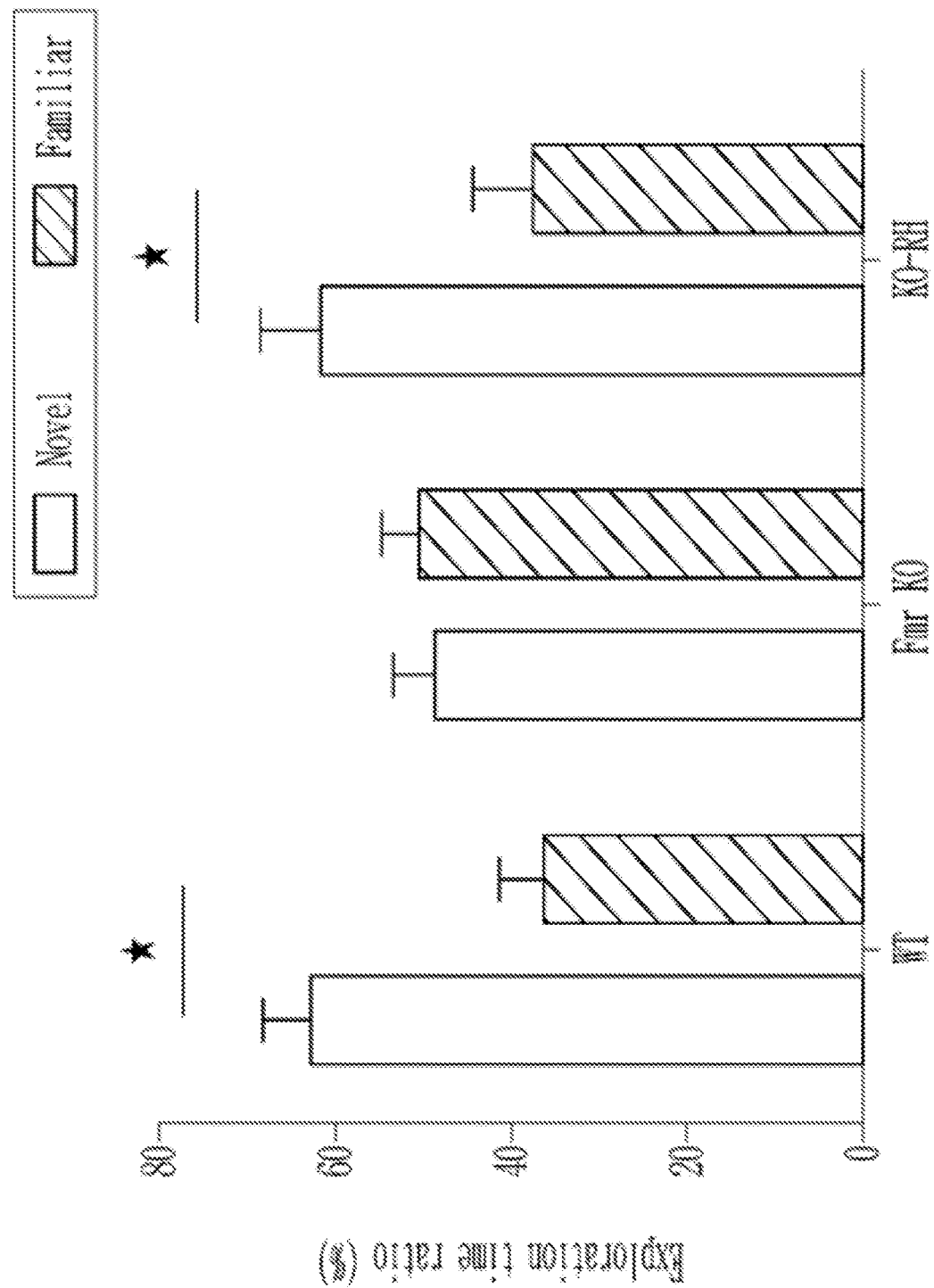
FIG. 1 is an analysis of the sociability improvement effect of rilmenidine in the animal model of fragile X syndrome (animal model deficient in Fmr1). It is determined to be social when the retention time for unfamiliar novel mice than existing familiar mice is longer. (WT: wild-type mice (normal control), Fmr KO: knock-out mice deficient in FMRP expression, KO-RH: group administered with rilmenidine to knock-out mice deficient in FMRP expression; *: P<0.05)

Hereinafter, the present invention will be described in more details.

As described above, fragile X syndrome is characterized by cognitive deficits in learning and memory, lack of social skills, communication difficulties, and hyperactivity; and can be accompanied by autism and attention deficit hyperactivity disorder, which are also developmental disorders. In addition, autism spectrum disorder is accompanied by symptoms such as hyperactivity, repetitive behaviors, or lack of social skills, and schizophrenia is accompanied by complex psychotic symptoms in various areas such as speech, behavior, emotion, and cognition that are related and derived from thinking disorder as the main pathology. However, drugs that can effectively treat these symptoms have not yet been reported.

Since rilmenidine according to the present invention shows a therapeutic effect on the direct or indirect symptoms (lack of sociability, prior wave suppression, etc.) of fragile X syndrome, any related developmental disorders, autism spectrum disorders, or schizophrenia, rilmenidine, a rilmenidine metabolite and a pharmaceutically acceptable salt thereof may be usefully used as active ingredients in pharmaceutical compositions for preventing and treating fragile X syndrome, any related developmental disorders, autism spectrum disorders, or schizophrenia.

Thus, the present invention can provide a pharmaceutical composition for preventing or treating fragile X syndrome (FXS), any developmental disorders related to fragile X syndrome, autism spectrum disorder, or schizophrenia, comprising rilmenidine, a rilmenidine metabolite, or a pharmaceutically acceptable salt thereof.

Rilmenidine, an active ingredient of the present composition for the prevention or treatment of fragile X syndrome, any related developmental disorders, autism spectrum disorder, or schizophrenia, may be a compound represented by the following chemical formula 1:

[Formula 1]

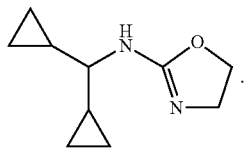

The molecular formula of rilmenidine is $C_{10}H_{16}N_2O$, and the molecular weight is 180.247 g/mol. The IUPAC name for rilmenidine is N-(dicyclopropylmethyl)-4,5-dihydro-1,3-oxazol-2-amine.

Rilmenidine of the present invention may include a rilmenidine hydrate, any rilmenidine derivatives, etc. within the range of having the same efficacy as rilmenidine, and may also include a solvate or any stereoisomer thereof. The method for obtaining rilmenidine is not particularly limited, and chemically synthesized or commercially available ones may be used using known methods.

In the present invention, the term "pharmaceutically acceptable salt" or "salt thereof" may be an acid addition salt formed with a free acid. Acid addition salts can be prepared by conventional methods, for example, by dissolving the compound in an aqueous solution of excess acid and precipitating the salt with a water-miscible organic solvent such as methanol, ethanol, acetone, or acetonitrile. In addition, equimolar amounts of the compound and acid or alcohol in water (e.g., glycol monomethyl ether) may be heated and then the mixture may be evaporated to dryness, or the precipitated salt may be filtered off with suction. An inorganic acid or an organic acid may be used as the free acid. Non-limiting examples of the inorganic acid include hydrochloric acid, phosphoric acid, sulfuric acid, nitric acid, tartaric acid, and the like, and these may be used alone or in a combination of two or more.

The salts of rilmenidine may include all salts of acidic or basic groups that may be present in the compounds of rilmenidine, unless otherwise indicated. For example, the salt of rilmenidine may include sodium, calcium, and potassium salts of a hydroxyl group, and other cosmetically acceptable salts of an amino group include hydrobromide, sulfuric acid, hydrogen sulfate, phosphate, and hydrogen phosphate, dihydrogen phosphate, acetate, succinate, citrate, tartrate, lactate, mandelate, methanesulfonate (mesylate) and p-toluenesulfonate (tosylate) salts, and it can be prepared through any salt preparation method known in the art.

In the present invention, "rilmeninine metabolite" or "metabolite thereof" refers to a product that is metabolized in the body of the subject to which rilmenidine is administered.

In the present invention, "prevention" means any action that suppresses the onset or delays the onset of the symptoms of the disease by administration of the composition. In the present invention, "improvement" or "treatment" refers to any action in which the symptoms of the disease are improved or beneficially changed by the administration of the composition.

In the present invention, "fragile X syndrome" or "fragile X syndrome-related developmental disorder" includes any one or more symptoms selected from the group consisting of repetitive behaviors, hyperactivity, reduced learning ability, lack of sociability, impulsivity, and anxiety symptoms, but not limited thereto, and can include any symptoms reported as symptoms of fragile X syndrome or fragile X syndrome-related developmental disorders.

In the present invention, "fragile X syndrome-related developmental disorder" preferably includes any one or more developmental disorders selected from the group consisting of attention deficit hyperactivity disorder (ADHD), autism spectrum disorder (ASD), intellectual disability, cognitive impairment, impulse control disorder, and anxiety disorder, but not limited thereto, and may include any symptoms that have been reported as a concomitant disorder or disease of fragile X syndrome.

In the present invention, "autism spectrum disorder" preferably includes any one or more symptoms selected from the group consisting of hyperactivity symptoms and social deficit symptoms, but is not limited thereto, and can include any symptoms that have been reported as symptoms of autism spectrum disorder.

The autism spectrum disorder may include autistic disorder, Rett's disorder, Asperger's syndrome, and Pervasive developmental disorder—not otherwise specified (PDD-NOS).

In a specific embodiment of the present invention, the present inventors confirmed the degree of improvement in sociability and improvement in pre-pulse suppression according to the presence or absence of administration of rilmenidine in a fragile X syndrome animal model (Fmr1-deficient animal model), a Cntnap2-deficient autistic animal model, an MK-801 drug-induced autism animal model, and an animal model of schizophrenia. As a result, it was confirmed that the effect of improving sociability and improving pre-pulse suppression appeared in mice treated with rilmenidine (FIGS. 1 to 5).

The composition of the present invention is used as a pharmaceutical preparation, the present composition may be formulated and administered in various oral or parenteral dosage forms at the time of clinical administration but is not limited thereto.

The oral administration may include, for example, tablets, pills, hard/soft capsules, solutions, suspensions, emulsifiers, syrups, granules, elixirs, and the like. These formulations may contain diluents (e.g., lactose, dextrose, sucrose, mannitol, sorbitol, cellulose, and/or glycine), or lubricants (e.g., silica, talc, stearic acid, and its magnesium or calcium salts and/or polyethylene glycol) in addition to an active ingredient. Tablets may also contain binders such as magnesium aluminum silicate, starch paste, gelatin, methylcellulose, sodium carboxymethylcellulose, and/or polyvinylpyrrolidone, optionally starch, agar, alginic acid, or its sodium salt. It may contain disintegrants or effervescent mixtures and/or absorbents, colorants, flavoring agents, and sweetening agents.

The present pharmaceutical composition containing rilmenidine, a rilmenidine metabolite, or a pharmaceutically acceptable salt thereof as an active ingredient, can be administered parenterally, and parenteral administration is by subcutaneous injection, intravenous injection, intramuscular injection, or intrathoracic injection. At this time, to formulate a dosage form for parenteral administration, a pharmaceutical composition containing rilmenidine or a pharmaceutically acceptable salt thereof as an active ingredient is mixed with water together with a stabilizer or buffer to prepare a solution or suspension, and it can be manufactured as an ampoule or vial unit dosage form. The composition may be sterilized and/or contain adjuvants such as preservatives, stabilizers, wetting agents or emulsification accelerators, salts and/or buffers for regulating osmotic pressure, and other therapeutically useful substances. It can be formulated according to the method of formulation or coating conventionally.

In the present composition, the dose of rilmenidine, a rilmenidine metabolite, or a salt thereof to the human body may vary depending on the patient's age, weight, sex, dosage form, health status, and disease level. Based on an adult patient weighing 60 kg, generally, 0.001 to 1,000 mg/day, preferably 0.01 to 500 mg/day, may be administered in divided doses once or several times a day at regular time intervals according to the judgment of a doctor or pharmacist.

The composition of the present invention may contain the active ingredient in an amount of 0.1 to 90% by weight based on the total weight of the composition. However, the content is not necessarily limited thereto and may vary depending on the patient's condition, the type of disease, and the degree of progression.

In another aspect, the present invention provides a health functional food composition for the prevention or improvement of fragile X syndrome (FXS), any fragile X syndrome-related developmental disorders, autism spectrum disorder or schizophrenia containing rilmenidine or a salt thereof as an active ingredient.

Specific details of the rilmenidine are the same as described above.

In the present invention, the term "health functional food" refers to food manufactured and processed in the form of tablets, capsules, powders, granules, liquids, pills, etc. using raw materials or ingredients useful for the human body. Here, 'functional' refers to obtaining useful effects for health purposes, such as regulating nutrients or physiological effects on the structure and function of the human body. The health functional food of the present invention can be prepared by a method commonly used in the art, and during the manufacture, it can be prepared by adding raw materials and components commonly added in the art. In addition, the dosage form of the health functional food may be manufactured without limitation as long as it is a dosage form recognized as a health functional food. The health functional food composition of the present invention has the advantage that there are no side effects that may occur during long-term administration using food as raw material, unlike general drugs, and has excellent portability, thereby it can be taken as a supplement to enhance the effect of alleviating the symptoms of fragile X syndrome or its related developmental disorders.

In the present health functional food composition for preventing or improving fragile X syndrome, any related developmental disorders, autism spectrum disorders, or schizophrenia, when rilmenidine is used as an additive in health functional food, it is added as it is or it can be used with food or food ingredients. They can be used together and can be used appropriately according to a conventional method. The mixing amount of the active ingredient may be appropriately determined according to each purpose of use, such as prevention, health, or treatment.

The formulation of health functional food may be in the form of powder, granules, pills, tablets, and capsules, as well as in the form of general food or beverages.

The type of food is not particularly limited, and examples of food to which the substance can be added include meat, sausage, bread, chocolate, candy, snacks, confectionery, pizza, ramen, other noodles, gum, and dairy products including ice cream, various soups, beverages, teas, drinks, alcoholic beverages, vitamin complexes, etc., and may include all foods in a conventional sense.

The mixing amount of the active ingredient may be appropriately determined depending on the purpose of its use (for prevention or improvement). In general, the amount of the compound (active ingredient) in the health food may be added in an amount of 0.1 to 90% by weight based on the total weight of the food. However, in the case of long-term intake for health and hygiene or health control, the amount may be less than the above range, and since there is no problem in terms of safety, the active ingredient may be used in an amount above the above range.

Beverages among functional foods according to the present invention may contain various flavoring agents or natural carbohydrates as additional ingredients like conventional beverages. The above-mentioned natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As for the sweetener, natural sweeteners such as taumatine and stevia extract, and synthetic sweeteners such as saccharin and aspartame may be used. The ratio of the natural carbohydrate may be about 0.01 to 0.04 g, preferably about 0.02 to 0.03 g per 100 mL of the beverage according to the present invention.

In addition to the above, the present health functional food for the prevention or improvement of fragile X syndrome, any related developmental disorders disorder or schizophrenia may include various nutrients, vitamins, electrolytes, flavoring agents, coloring agents, pectic acid and its salts, alginic acid, and its salts, organic acids, and protective properties. It may contain colloidal thickeners, pH adjusters, stabilizers, preservatives, glycerin, alcohols, and carbonating agents used in carbonated beverages. In addition, the present health functional food composition for preventing or improving fragile X syndrome, any related developmental disorders or schizophrenia may contain fruit for the production of natural fruit juice, fruit juice beverage, and vegetable beverage. These components may be used independently or in combination. The ratio of these additives is not limited but is generally selected in the range of 0.01 to 0.1 parts by weight relative to 100 parts by weight of the present health functional food.

Hereinafter, the present invention will be described in more detail through examples. These examples are only for illustrating the present invention, and it will be apparent to those of ordinary skill in the art that the scope of the present invention is not to be construed as being limited by these examples.

Example 1: Confirmation of the Improvement Effect of Sociability and the Improvement Effect of Pre-Pulse Suppression by Rilmenidine in the Fragile X Syndrome Animal Model Preparation of Laboratory Animals and Drugs Purchased a 5-week-old Fmr 1 knockout mouse (Jackson Laboratory, USA) weighing about 22 g to 24 g, and acclimatized to an environment with a temperature of 23±2° C. and humidity of 55±10% and a light-dark cycle of 12 hours while allowing them to freely consume water and feed. After breeding (Konkuk University Laboratory Animal Center), they were used for experiments. For all animals, wild-type (WT) with normal FMRP expression and male KO mice lacking FMRP (Fragile X mental retardation protein) expression (which induces Fragile X Syndrome (FXS)) were used. Dosing and experiments were performed according to the age of the week. Dosing was performed at the same time. Behavioral experiments were conducted 30 minutes after administration. It was divided into groups administered with 1 mg/kg each of rilmenidine (Sigma Aldrich) in FMRP expression-deficient knock-out (Knock-Out) mice, wild-type (Wild Type) mice, and 0.25 DMSO in FMRP expression-deficient knock-out mice (6 mice per group). For the drug administration group, rilmenidine was dissolved in 0.25% DMSO and then administered intraperitoneally at a dose of 50 ug/kg. Meanwhile, 0.25% DMSO was intraperitoneally administered to the control group.

Confirmation of Sociability Improvement Effect of Rilmenidine in Fragile X Syndrome Experimental Animals To confirm the therapeutic effect of rilmenidine on social deficits, one of the phenotypes of fragile X syndrome and related developmental disorders, a three-chamber test was performed in the Fmr1-deficient animal model. If the animal model spent more time with a novel mouse rather than a familiar mouse, it is judged to be social. The test animal was exposed to the stimulus mouse for 10 minutes, and then to a new stimulus mouse (novel) for another 10 minutes. In this case, the old mouse is called familiar and the new mouse is called novel. The time the test mouse explored each stimulus mouse was measured and expressed as %. As a result of the experiment, it was confirmed that the wild-type mouse spent more time with the novel mouse than the familiar mouse, indicating normal sociability. On the other hand, the mouse deficient in Fmr 1 spent more time with the familiar mouse than the novel mouse, indicating impaired sociability. When Fmr1-deficient mouse was treated with rilmenidine, more time was spent with the novel mouse than with the familiar mouse, indicating that sociability was improved through the treatment with rilmenidine (FIG. 1).

Example 2: Confirmation of the Improvement Effect of Pre-Pulse Suppression by Rilmenidine in the Animal Models of Autism and Schizophrenia (Animal Models Induced with MK-801 Drug)

Confirmation of Improvement Effect of Pre-Pulse Suppression of Rilmenidine

Figure 2:
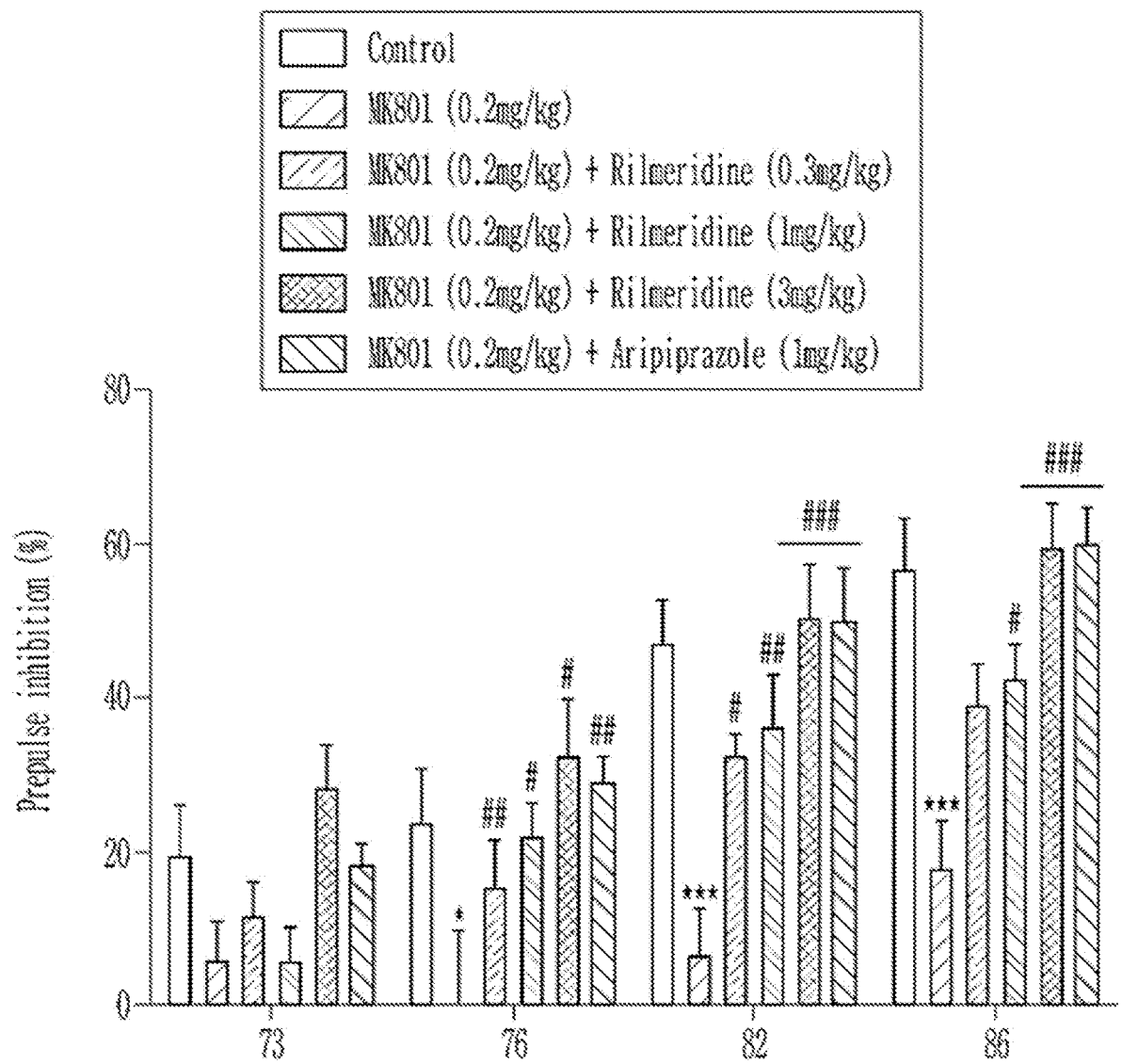
FIG. 2 is an analysis of the improvement effect of pre-wave suppression of rilmedinin in the animal model treated with MK-801 in wild-type mice. (*: difference from normal control group, P<0.05, ***: difference from normal control group, P<0.0001; #, ##, ###: difference from MK801 treatment group, #P<0.05, ##P<0.01, ###P<0.001)

The startle response was confirmed in an animal model treated with MK-801 in wild-type mice. Mice were divided into groups, and 0.9% physiological saline (saline solution), rilmenidine, or a positive control drug (aripiprazole) was intraperitoneally administered to each group. Then, sensorimotor gating was evaluated through a pre-wave suppression test (converted using Equation 1). As a result of the experiment, it was confirmed that the pre-pulse suppression was reduced when wild-type mice were treated with MK-801, but the reduced pre-pulse suppression was restored when MK-801 was treated and then treated with rilmenidine (FIG. 2).

Pre-pulse suppression (%)=100−[(startle response to pre-stimulus+stimulus)/(startle response to stimulus)]*100  [Equation 1]

Confirmation of Cognitive Improvement Effect of Rilmenidine

The cognitive improvement effect of rilmenidine was confirmed using an animal model treated with MK-801 in wild-type mice. The experiment was a novel object recognition test, where two identical objects were placed in the same location and trained, and 24 hours later, one identical object (familiar) and the other new object (novel) were put in, and the cognitive ability of the animal was tested by evaluating whether they could distinguish between familiar and new objects.

Figure 3:
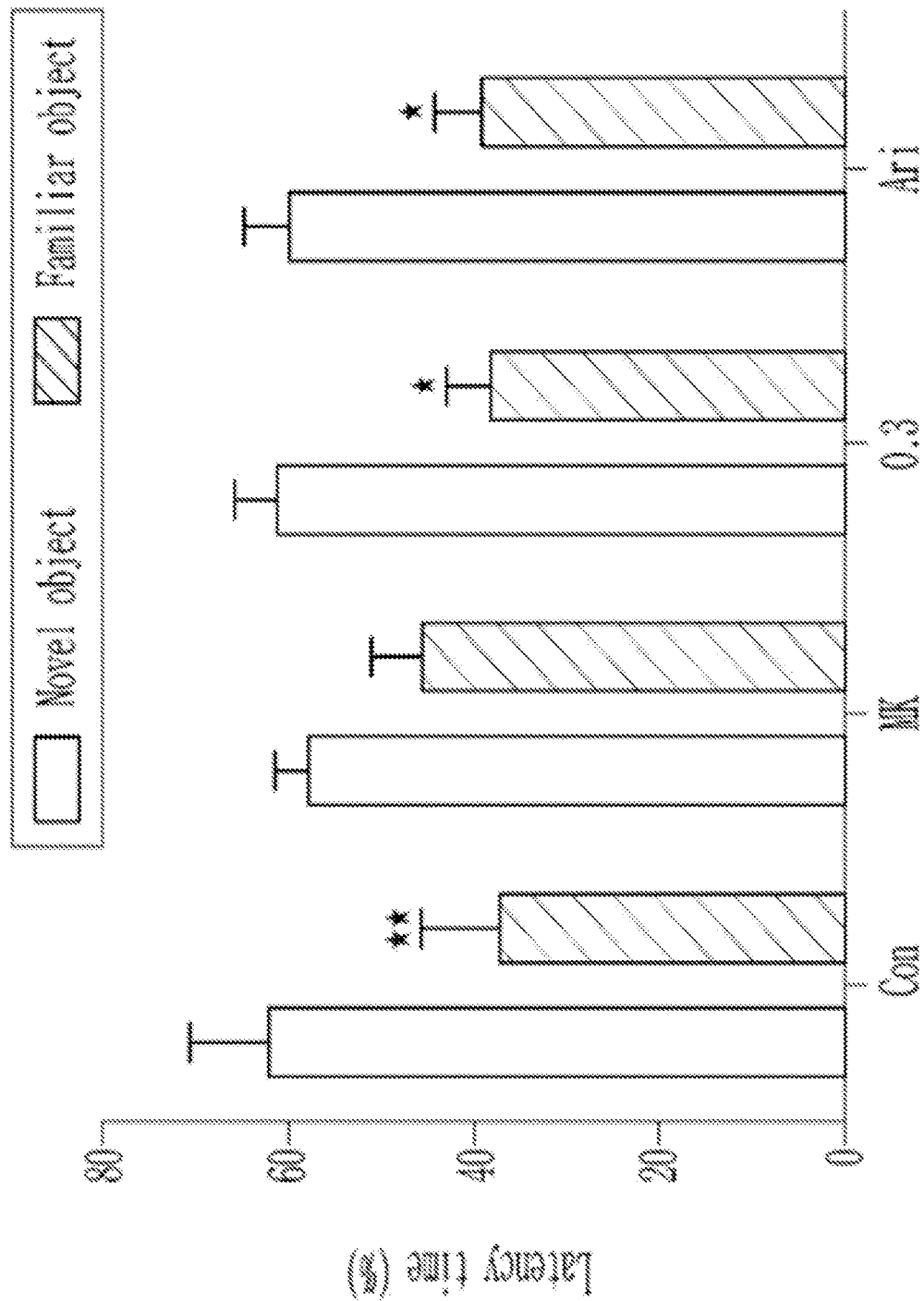
FIG. 3 is an analysis of the cognitive improvement effect of rilmenidine in the animal model treated with MK-801 in wild-type mice. (Con: normal control group, MK: MK-801 treatment group, 0.3:0.3 mg/kg of rilmenidine treatment group, Ari: positive control drug (aripiprazole treatment group); *: difference between novel object and familiar object P<0.05, **: Difference between novel object and familiar object P<0.01)

As a result of the experiment, when wild-type mice were treated with MK-801, the ability to distinguish existing familiar objects from new novel objects was reduced. However, the ability to distinguish novel objects was improved when MK-801 was treated and then treated with rilmenidine, indicating that rilmenidine has a cognitive improvement effect (FIG. 3).

Example 3: Confirmation of the Improvement Effect of Sociability by Rilmenidine in Autism Animal Model (Cntnap2 Deficient Animal Model)

To confirm the therapeutic effect of rilmenidine on social deficits, one of the phenotypes of developmental disorders, a three-chamber test was performed using an animal model lacking Cntnap2.

Figure 4:
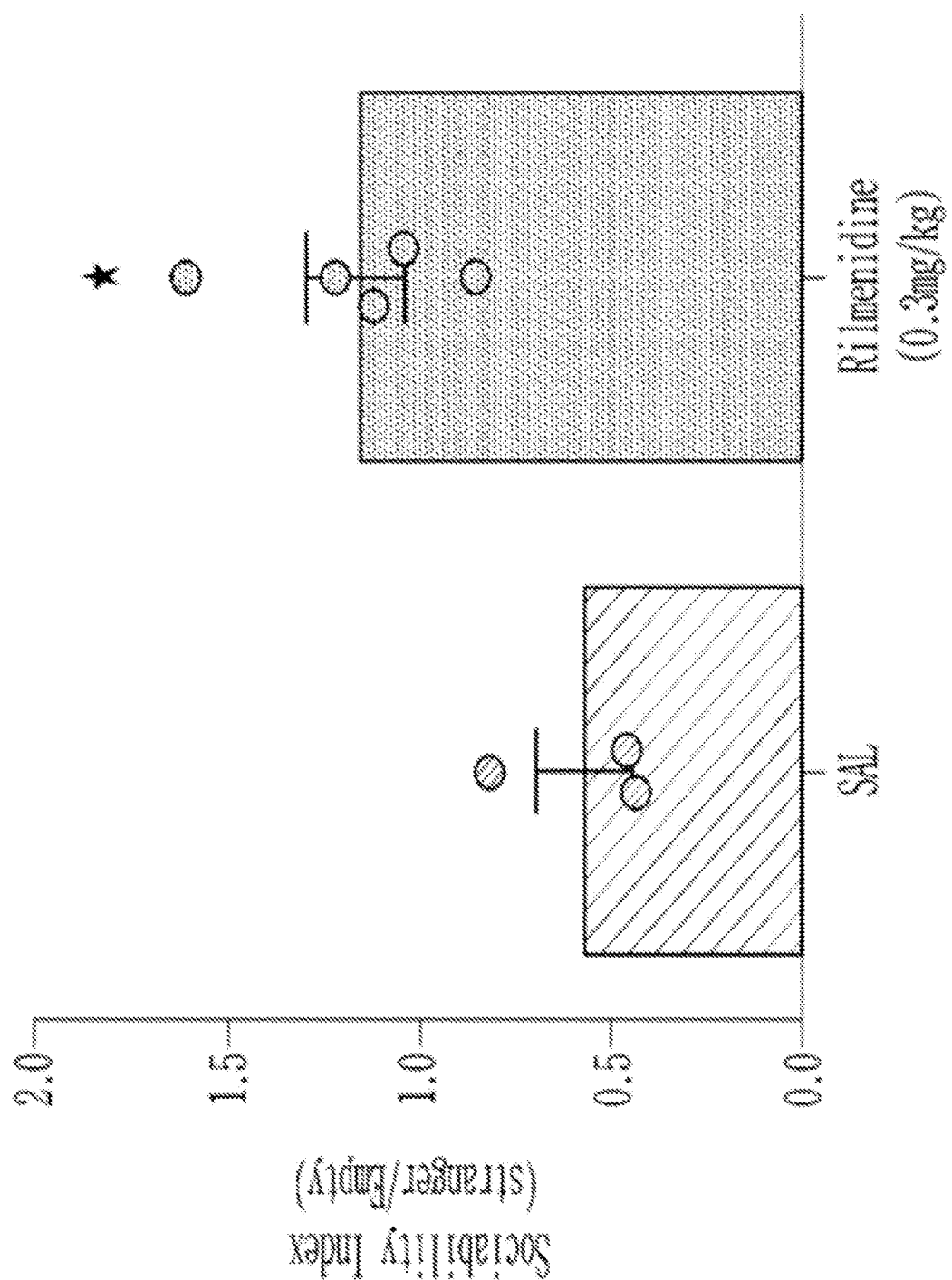
FIG. 4 is an analysis of the sociability improvement effect of rilmenidine in an autistic animal model (Cntnap2-deficient autistic animal model). It is determined to be social when the retention time for strange mice is longer than the empty space. The Y-axis sociability index of the graph is the value obtained by dividing stranger (retention time for mice) by empty (retention time for empty space). (SAL: knock-out mice deficient in Cntnap2 expression, rilmenidine: group administered rilmenidine to knock-out mice deficient in Cntnap2 expression; *: difference from SAL, P<0.05)

The sociability index of FIG. 4 represents a value obtained by dividing stranger (retention time for a mouse) by empty (retention time for an empty space). As a result of the experiment, in the case of the mouse deficient in Cntnap2, the retention time for the empty space was longer than the retention time for the mouse, indicating that sociability was reduced due to the Cntnap2 deficiency. On the other hand, when Cntnap2-deficient mice were treated with rilmenidine, it was confirmed that the retention time for the mouse was longer than the retention time for the empty space, indicating that rilmenidine treatment can improve sociability (FIG. 4).

Figure 5:
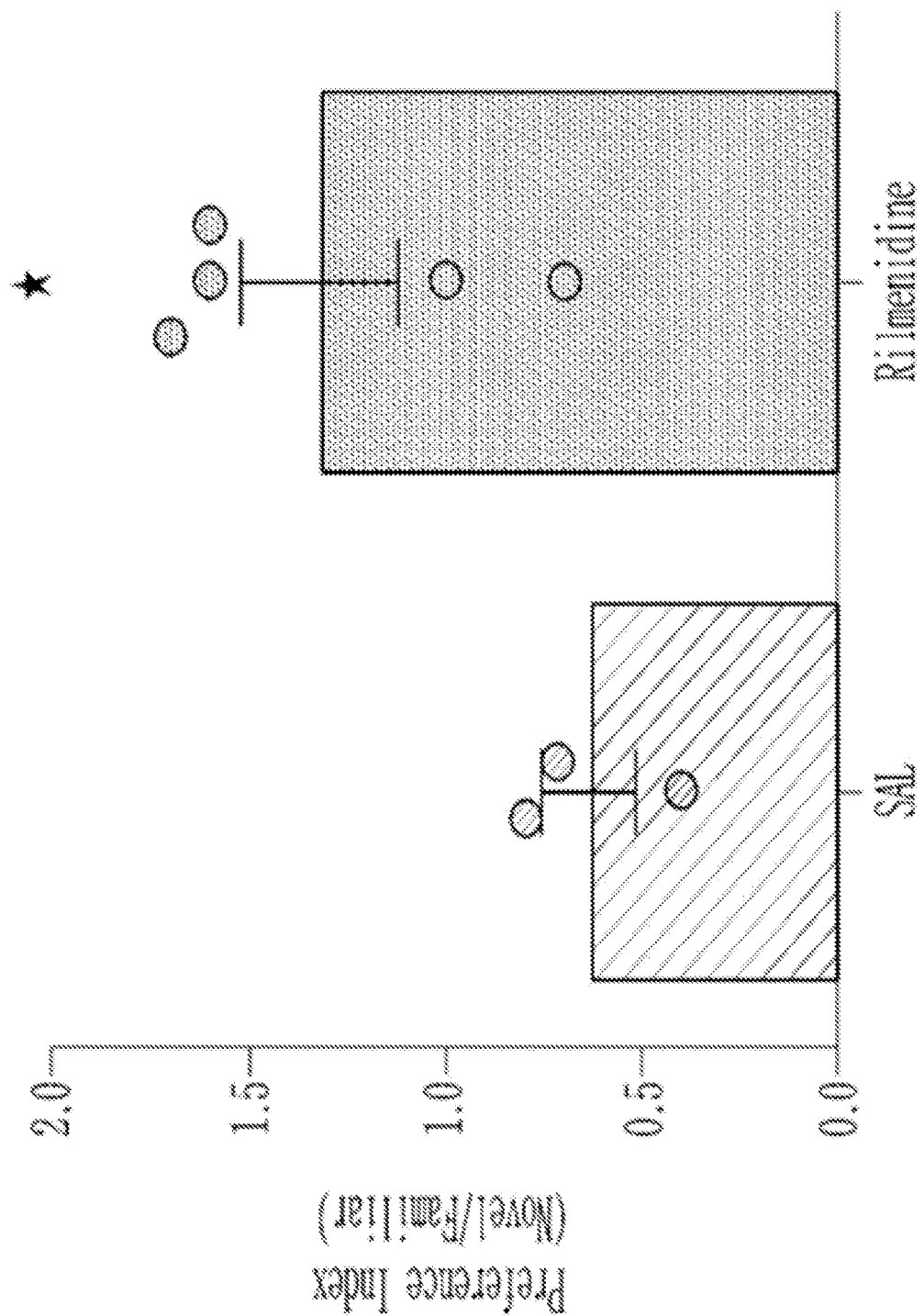
FIG. 5 is an analysis of the effect of rilmenidine on improving social preference in the autistic animal model (Cntnap2-deficient autistic animal model). It is determined to be social when the residence time for unfamiliar novel mice than existing familiar mice is longer. (SAL: knock-out mice deficient in Cntnap2 expression, rilmenidine: group administered rilmenidine to knock-out mice deficient in Cntnap2 expression; *: difference from SAL, P<0.05)

FIG. 5 is a result of evaluating whether or not the time spent with a novel mouse is longer than that of a familiar mouse after exploring a stimulus mouse (familiar) for 10 minutes in the experimental animal, and after adding a new stimulus mouse (novel) together for 10 minutes. In this case, the old mouse is called familiar, and the new mouse is called novel. If the animal model spent more time with a novel mouse rather than a familiar mouse, it is judged to be social. Experimental results were expressed as a preference index by measuring the time the test mouse explores each mouse or the sniffing time to each mouse. The higher the preference index, the more time spent with the novel mouse than with the familiar mouse, or the more time spent sniffing with the novel mouse than with the familiar mouse. As a result of the experiment, Cntnap2-deficient mouse spent more time or sniffed more with the familiar mouse than the novel mouse, indicating that Cntnap2 deficiency reduced sociability. On the other hand, when Cntnap2-deficient mice were treated with rilmenidine, they spent more time and sniffed more with the novel mouse than the familiar mouse, indicating the increase in preference index. Through this, it was confirmed that rilmenidine treatment can improve sociability (FIG. 5).

Hereinafter, an example of the preparation of a pharmaceutical or food composition containing rilmenidine as an active ingredient according to the present invention will be described, not intended to limit the invention but merely to describe it in details. Using the active ingredient, the pharmaceutical or food composition of Preparation Example 1 or 2 was prepared according to a conventional method according to the following compositional components and composition ratios.

[Preparation Example 1] Preparation of Pharmaceutical Composition

<1-1> Preparation of Powder
Rilmenidine 20 mg
Lactose hydrate 100 mg
Talc 10 mg

The above ingredients were mixed and filled in an airtight bag to prepare a powder.

<1-2> Preparation of Tablets

Rilmenidine 10 mg
Corn Starch 100 mg
Lactose hydrate 100 mg
Magnesium stearate 2 mg After mixing the above ingredients, tablets were prepared by tableting according to a conventional manufacturing method of tablets.

<1-3> Preparation of Capsules

Rilmenidine 10 mg
Microcrystalline Cellulose 3 mg
Lactose hydrate 14.8 mg Magnesium stearate 0.2 mg After mixing the above ingredients, the capsules were prepared by filling in gelatin capsules according to a conventional manufacturing method of capsules.

<1-4> Preparation of Injection

Rilmenidine 10 mg
Mannitol 180 mg
Sterile distilled water for injection 2974 mg
Sodium monohydrogen phosphate 26 mg After mixing the above ingredients, the content of the above components per 1 ampoule (2 mL) was prepared according to a conventional method for preparing injections.

<1-5> Preparation of Liquid Preparation

Rilmenidine 10 mg
Isomerized sugar 10 mg
Mannitol 5 mg
Purified water appropriate amount
Lemon flavored appropriate amount The above ingredients were dissolved by adding each ingredient to purified water according to a conventional manufacturing method. After adding an appropriate amount of lemon flavor, purified water was added to adjust the total volume to 100 mL, sterilized, and filled in a brown bottle to prepare a solution.

[Production Example 2] Preparation of Health Functional Food

<2-1> Manufacturing of Health Supplements

Rilmenidine 10 mg
Vitamin mixture appropriate amount
Vitamin A acetate 70 μg
Vitamin E 1.0 mg
Vitamin $B_1$ 0.13 mg
Vitamin B 20.15 mg
Vitamin B 60.5 mg
Vitamin $B_{12}$ 0.2 μg
Vitamin C 10 mg
Biotin 10 μg
Nicotinamide 1.7 mg
Folic acid 50 μg
Calcium pantothenate 0.5 mg
Mineral mixture appropriate amount
Ferrous sulfate 1.75 mg
Zinc oxide 0.82 mg
Magnesium carbonate 25.3 mg
Potassium monophosphate 15 mg
Dibasic calcium phosphate 55 mg
Potassium citrate 30 mg
Calcium carbonate 100 mg
Magnesium chloride 24.8 mg The composition ratio of the vitamin and mineral mixture is relatively suitable for health food in a preferred embodiment, but the mixing ratio may be arbitrarily modified to prepare granules and can be used for preparing health food compositions according to a conventional method.

<2-2> Manufacturing of Health Drinks

Rilmenidine 10 mg
Vitamin C 15 g
Vitamin E (powder) 100 g
Iron lactate 19.75 g
Zinc oxide 3.5 g
Nicotinic acid amide 3.5 g
Vitamin A 0.2 g
Vitamin B1 0.25 g
Vitamin B2 0.3 g
Purified water quantity After mixing the above ingredients according to a conventional health drink manufacturing method, stirring and heating at 85° C. for about 1 hour, the resulting solution was filtered and obtained in a sterilized 2 L container, sealed, sterilized, refrigerated, and then used in the manufacture of health beverage compositions.

Although the composition ratio is prepared by mixing ingredients suitable for relatively favorite beverages in a preferred embodiment, the mixing ratio may be arbitrarily modified according to regional and national preferences such as demand class, demanding country, and use.

The above description of the present invention is for illustration, and those of ordinary skill in the art to which the present invention pertains can understand that it can be easily modified into other specific forms without changing the technical spirit or essential features of the present invention. will be. Therefore, it should be understood that the embodiments described above are illustrative in all respects and not restrictive.

The invention claimed is:

1. A method for treating fragile X syndrome (FXS), fragile X syndrome-related developmental disorders, autism spectrum disorder, or schizophrenia, comprising the administration of rilmenidine, or a pharmaceutically acceptable salt thereof to a subject in need thereof.

2. The method according to claim 1, wherein the rilmenidine is represented by the following formula (1):

[Formula 1]

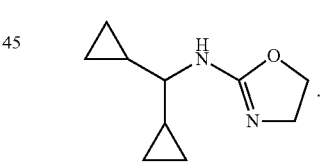

3. The method according to claim 1, wherein the fragile X syndrome is accompanied by one or more symptoms selected from the group consisting of repetitive behaviors, hyperactivity, reduced learning ability, lack of sociability, impulsivity, and anxiety symptoms.

4. The method according to claim 1, wherein the fragile X syndrome-related developmental disorder includes one or more symptoms selected from the group consisting of attention deficit hyperactivity disorder (ADHD), autism spectrum disorder (ASD), intellectual disability, cognitive impairment, impulse control disorder and anxiety disorder.

5. The method according to claim 1, wherein the autism spectrum disorder is accompanied by one or more symptoms selected from hyperactivity or social deficit.

* * * * *